United States Patent [19]

Schiehser et al.

[11] Patent Number: 4,490,527

[45] Date of Patent: Dec. 25, 1984

[54] BENZO-FUSED HETEROCYCLIC ANTI-ULCER AGENTS

[75] Inventors: Guy A. Schiehser, Malvern; Donald P. Strike, St. Davids, both of Pa.

[73] Assignee: American Home Products Corporation, New York, N.Y.

[21] Appl. No.: 468,221

[22] Filed: Feb. 22, 1983

Related U.S. Application Data

[63] Continuation-in-part of Ser. No. 431,879, Sep. 30, 1982, abandoned, which is a continuation-in-part of Ser. No. 330,403, Dec. 14, 1981, abandoned.

[51] Int. Cl.$^3$ .......................................... C07D 279/12
[52] U.S. Cl. .................................. 544/62; 544/61; 544/133; 544/135; 544/144; 546/198; 546/200; 548/181; 548/212; 548/453; 548/467; 548/471
[58] Field of Search ............... 548/212, 453, 471, 181, 548/467; 544/144, 133, 135, 61, 62; 546/198, 200

[56] References Cited

U.S. PATENT DOCUMENTS 4,325,963  4/1982  Hitzel et al. ................. 548/453 X

*Primary Examiner*—Richard A. Schwartz
*Attorney, Agent, or Firm*—George Tarnowski

[57] ABSTRACT

Compounds of the formula:

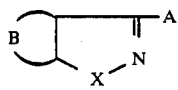

wherein B is a moiety having the formula:

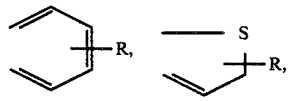

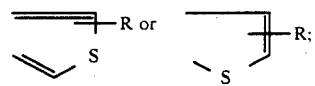

R is mono- or dihalo, amino, nitro, cyano, hydroxy, trifluoromethyl, mercapto, lower alkyl, lower alkoxy, alkanoyl, cycloalkyl of 4–7 carbon atoms, carboxy, alkoxycarbonyl, mono- or di-lower alkyl substituted amino, alkanoylamino, lower alkyl thio, lower alkylsulfonyl, sulfamoyl, lower alkyl substituted sulfamoyl, phenyl or phenyl substituted with halo, lower alkyl, lower alkoxy, trifluoromethyl, hydroxy, amino, cyano or nitro.

X is $SO_2$, SO, S or C=O; and

A is amine selected from the group

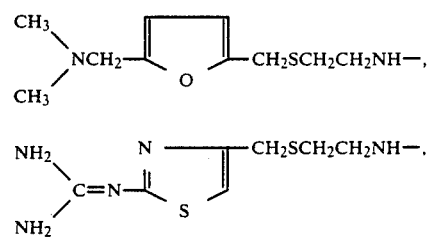

or

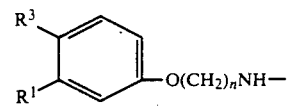

wherein n = 1–4, wherein $R^1$ is hydrogen or $R^2CH_2$ wherein $R^2$ is mono- or diloweralkylamino, mono- or di-N-lower alkylaminoloweralkyl, (2-furyl)methylamino, benzylamino, lowercycloalkylamino, 1-pyrrolidinyl, 1-piperidinyl, 1-hexahydroazepinyl, 1-octahydroazocinyl, 3-thiazolidinyl, 4-morpholinyl or 4-thiomorpholinyl; $R^3$ is hydrogen or (1-piperidinyl)methyl with the proviso that when $R^3$ is (1-piperidinyl)methyl, $R^1$ is hydrogen; n is 1 to 4, and the pharmacologically acceptable salts thereof.

41 Claims, No Drawings

BENZO-FUSED HETEROCYCLIC ANTI-ULCER AGENTS

This is a continuation-in-part application of U.S. Ser. No. 431,879, filed Sept. 30, 1982, now abandoned, which is a continuation-in-part of Ser. No. 330,403 filed Dec. 14, 1981, now abandoned.

This invention relates to new benzo-fused heterocyclic compounds having a selective action on $H_2$ histamine receptors and which inhibit gastric acid secretion.

It has been postulated that the physiologically active compound histamine, which occurs naturally within the animal body, is able to combine, in the course of exerting its activity, with certain specific receptors of which there are at least two distinct and separate types. The first has been named the $H_1$ receptor (Ash and Schild, Brit. J. Pharmac., 1966, 27,427) and the action of histamine at this receptor is blocked (antagonized) by classical "antihistamine" drugs such as mepyramine (pyrilamine). The second histamine receptor has been named the $H_2$ receptor (Black et al., Nature, 1972,236, 385) and the action of histamine at this receptor is blocked by drugs such as cimetidine. It is known that one of the results of the blockage of the action of histamine at the $H_2$ receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

The commercialization of cimetidine and subsequent follow-up pharmacological research in patients has demonstrated that cimetidine is a drug with limitations, such as short duration of action, anti-androgenic activity, and a tendency to cause confusional states in elderly patients. Obviously, much intensive research has been carried out to find improved $H_2$ antagonists. Indeed, selective $H_2$ antagonists having greater activity than cimetidine have been discovered. Among the better known new $H_2$ antagonists are ranitidine (disclosed in U.S. Patent No. 4,128,658) having the structure:

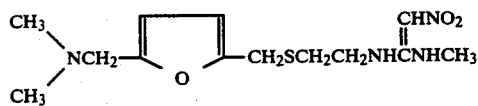

tiotidine (U.S. Pat. No. 4,165,378) having the structure:

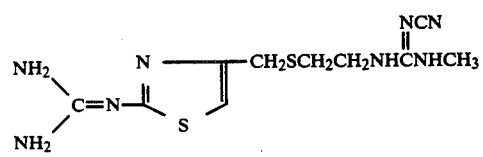

and compounds such as those disclosed in European Patent Application No. 24,510 having the structure:

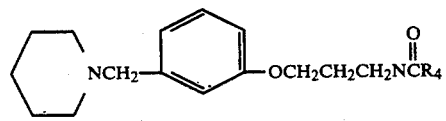

wherein $R_4$ is among others, hydrogen, methyl or methylol and those disclosed in U.K. Pat. No. 2,067,987 having the structure:

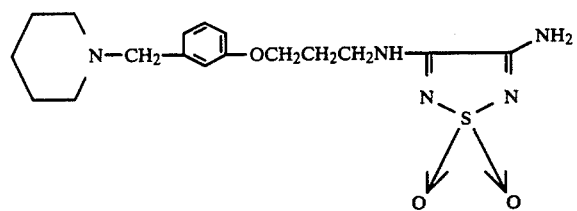

There has now been discovered a novel group of compounds, with potent $H_2$ receptor antagonist activity, having the following formula:

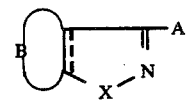

wherein B is a moiety having the formula:

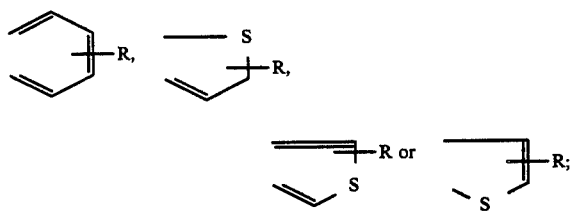

R is mono- or dihalo, amino, nitro, cyano, hydroxy, trifluoromethyl, mercapto, lower alkyl, lower alkoxy, alkanoyl, lowercycloalkyl, carboxy, alkoxycarbonyl, mono- or di-lower alkyl substituted amino, alkanoylamino, lower alkyl thio, loweralkyl-sulfonyl, sulfamoyl, lower alkyl substituted sulfamoyl, phenyl or phenyl substituted with halo, lower alkyl, lower alkoxy, trifluoromethyl, hydroxy, amino, cyano or nitro; X is $SO_2$, SO, S, or C=O and A is an amine selected from the group:

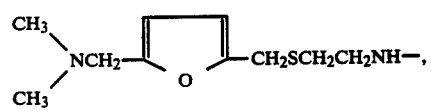

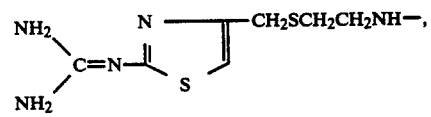

or

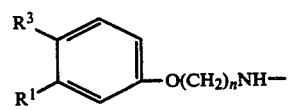

wherein $R^1$ is hydrogen or $R^2CH_2$ wherein $R_2$ is mono- or diloweralkylamino, mono- or di-N-loweralkylamino-lower alkyl, (2-furyl)methylamino, benzylamino, lower cycloalkylamino, 1-pyrrolidinyl, 1-piperidinyl, 1-hexahydroazepinyl, 1-octahydroazocinyl, 3-thiazolidinyl, 4-morpholinyl or 4-thiomorpholinyl; $R^3$ is hydrogen or (1-piperidinyl)methyl, with the proviso that when $R^3$ is (1-piperidinyl)methyl, $R^1$ is hydrogen; n is 1 to 4, and the pharmacologically acceptable salts thereof.

The term "halo" refers to fluoro, chloro and bromo. The terms "lower alkyl" and "lower alkoxy" refer to moieties having 1–6 carbon atoms in the carbon chain. The term "lower cycloalkyl" refers to cyclic structures having 5 to 7 carbon atoms. The term "alkanoyl" refers to the moiety RCO- wherein R is an alkyl group having 1–4 carbon atoms.

The compounds of the invention can be readily prepared by reacting the chloride of an appropriate benzisothiazole or a derivative thereof, a 3-(methylthio)-thienoisothiazole-1,1-dioxide or an appropriate derivative thereof or isoindolinone chloride with the desired amine according to the following reaction sequence:

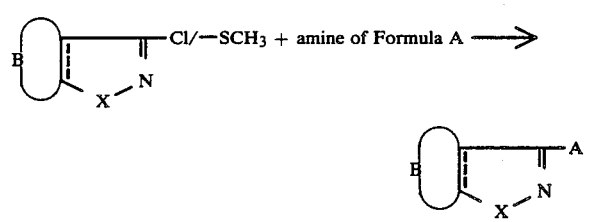

where B, R, X and A are as defined hereinbefore. The benzisothiazole and isoindolinone chlorides are known compounds which are readily available or which can be prepared by known methods. Thus, for example, the compound

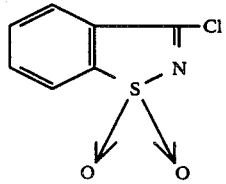

is pseudo saccharin chloride, and can be prepared according to the method of Stephen et al., J. Chem. Soc., 1975, 490–92. The 3-(methylthio)thienoisothiazoles can be prepared according to the following reaction sequence exemplified for 3-(methylthio)thieno[3,4-d]isothiazole-1,1-dioxide:

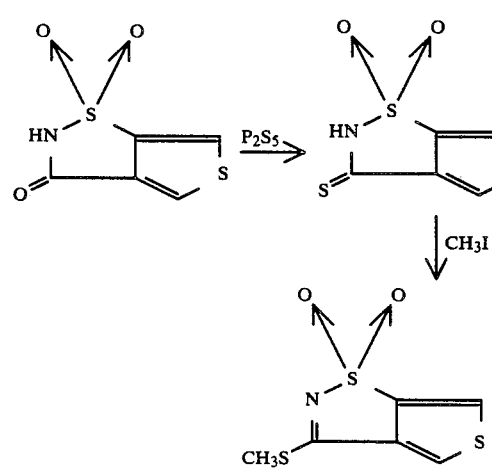

The starting compound thieno[3,4-d]isothiazol-3(2H)-one-1,1-dioxide can be prepared according to the procedure of P.A. Rossy et al., J. Org. Chem., 45, 617 (1980). The amines of formula A are well-known in the field of $H_2$-receptor antagonists and their preparation is reported in the following patent literature:

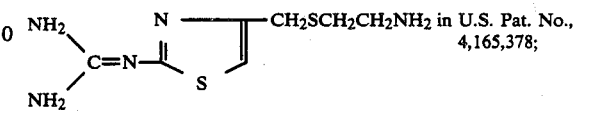

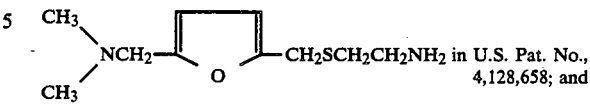

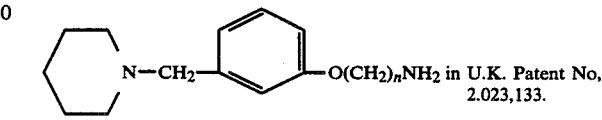

The amines having the formula

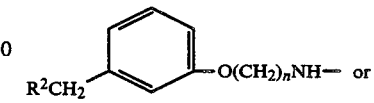

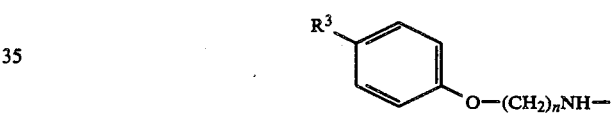

wherein $R^2$, $R^3$ and n are as defined hereinbefore, can be prepared according to the following reaction sequence:

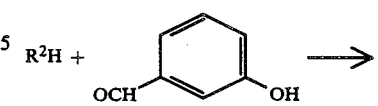

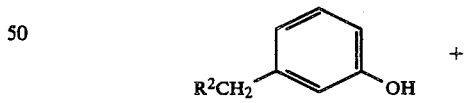

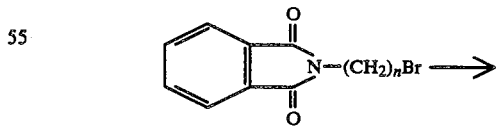

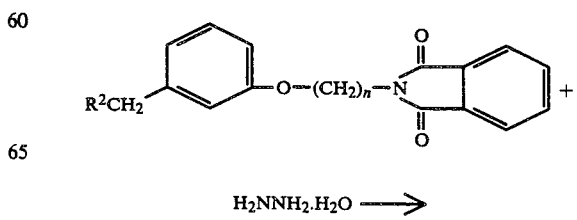

-continued

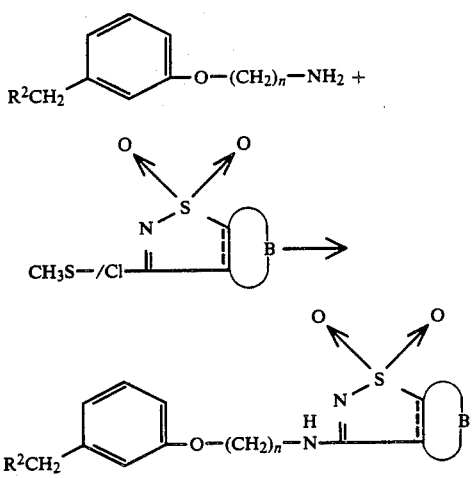

As an alternative procedure, the preparation of the isoindoledione reactant can be carried out as follows:

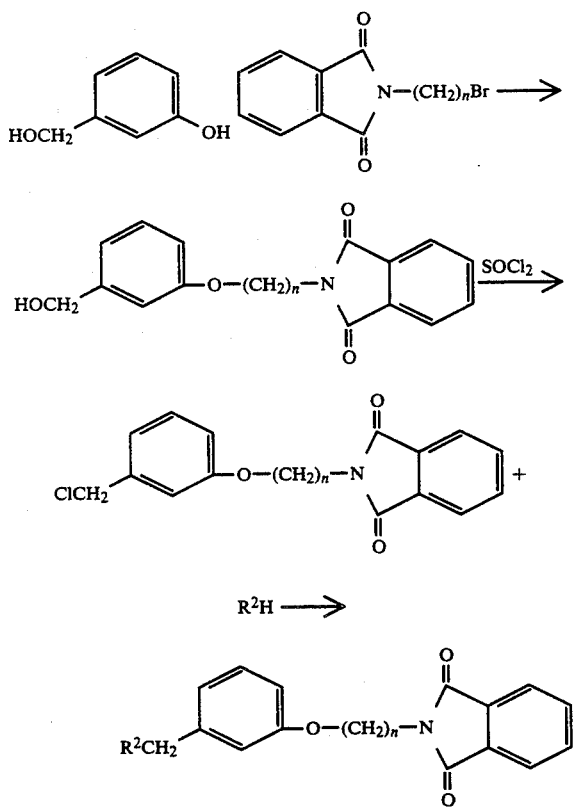

The compounds of the invention readily form pharmacologically acceptable salts with both inorganic and organic acids, such as hydrochloric, hydrobromic, sulfuric, nitric, phosphoric, acetic, maleic, fumaric, citric and the like.

The compounds of the invention have potent histamine $H_2$-blocking activity and can be used in the treatment of conditions where there is hypersecretion of gastric acid, such as in gastric and peptic ulceration, and other conditions caused or exacerbated by gastic acidity such as stress ulceration or gastric intestinal bleeding due to trauma.

The compounds of the invention can be administered orally or parenterally or by suppository, of which the preferred route is the oral route. They may be used in the form of the base or as a pharmacologically acceptable salt. They will in general be associated with a pharmaceutically acceptable carrier or diluent, to provide a pharmaceutical composition.

The compounds of the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form.

A convenient daily dose by the oral route would be of the order of 100 mg to 1.2 g per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

The histamine $H_2$-antagonist activity of the compounds of the invention may be demonstrated by the ability of the compounds to inhibit the histamine-induced positive chronotropic response in the spontaneously beating right atrium of the guinea pig heart, as well as by activity in other more generalized procedures, such as the modified Shay procedure of pylorus ligation for the study of rat gastric secretion and by the study of gastric scretion in the unanesthetized dog. The procedures for these tests and the results for some of the compounds of the invention are presented at the end of the following examples, which will serve to illustrate the present invention.

PREPARATION A

Preparation of 3-chlorobenzisothiazole-1,1-dioxide (ψ-saccharin chloride)

Following the procedure of Stephen et al., J. Chem. Soc., 1957, 490–92, 1 mol of saccharin (1,2-benzisothiazol-3(2H)-one 1,1-dioxide) is heated with 1.1 mol phosphorus pentachloride at 170° C. for 1.5 hours. Phosphorus oxychloride is removed at 60°/30 mm and the yellow crystalline residue of ψ-saccharin chloride and o-cyanobenzene sulfonyl chloride is treated with ether in which the latter is soluble. The sparingly soluble ψ-saccharin chloride in a yield of 28% is collected and crystallized from ether as white needles, m.p. 132°–137° C.

PREPARATION B

Preparation of 3-Chloro-1H-isoindol-1-one

Following the procedure of U.K. Pat. No. 704,595, 147 parts of phthalimide are refluxed while stirring with 208 parts of phosphorus pentachloride and 150 parts of o-dichlorobenzene. A light orange-yellow solution is formed at 130° C. and the solution is stirred at 150° C. for a 4 hour period. The phosphorus oxychloride produced is distilled off under reflux up to an internal temperature at 205° C. and the o-dichlorobenzne is partly distilled in vacuo. After removing the o-dichlorobenzene and the first runnings from 105° C. to about 143° C. (under 15 mm pressure) about 50 parts of an almost colorless distillate are obtained. Redistilling the solution produces a colorless distillate (b.p. 159°–160° C./15 mm) which solidifies at 70°–73° C. as fine crystals. The product is recrystallized from dry cyclohexane to yeild the title compound in long bright needles having a melting point of 77°-78° C.

PREPARATION C

Preparation of 3-(Methylthio)Thieno-[3,4-d]Isothiazole-1,1-Dioxide

A. Thieno-[3,4-d]Isothiazol-3(2H)-Thione-1,1-Dioxide

To a mixture of 5.6 g. (0.03 mole) of thieno[3,4-d]isothiazol-3(2H)-one-1,1-dioxide in 50 ml. of dry pyridine is added 5.6 g. (0.016 mole) of phosphorus pentasulfide portionwise over 3 minutes. The viscous mixture is slowly heated in an oil bath under an atmosphere of nitrogen. The temperature of the oil bath is slowly increased to 80° C. after 30 minutes. The temperature of the oil bath is then kept at 80° C. for 25 minutes, the internal temperature reading 63° C. The solution is cooled to 50° C. and is added dropwise over 5 minutes to 200 ml. of water and cooled in an ice bath. The precipitate which forms is collected and discarded. The filtrate is cooled in ice and acidified with concentrated hydrochloric acid to pH 1. The precipitate which forms is collected to yield 40% of material. In another experiment, a sample is recrystallized from water to obtain an analytical sample, m.p. 196°-8° (dec.).

Analysis for: $C_5H_3NO_2S_3$, Calculated: C, 29.26; H, 1.47; N, 6.82, Found: C, 29.91; H, 1.43; N, 6.87.

B. 3-(Methylthio)Thieno[3,4-d]Isothiazole-1,1-Dioxide

To a mixture of 0.9 g. (0.0044 mole) of thieno[3,4-d]isothiazol-3(2H)-thione-1,1-dioxide in 4 ml. of ethanol is added a solution of 0.35 g. (0.0044 mole) of 50% sodium hydroxide in 3 ml. of water. To this thick mixture is added 0.62 g. (0.0044 mole) of iodomethane. The mixture is heated under reflux for 5 minutes, and then filtered to give 0.35 g. of product. On cooling, a second crop of 0.1 g. of material is obtained. A small amount of the first crop is recrystallized from ethanol to afford an analytical sample, m.p. 184°-6°.

Analysis for: $C_6H_5NO_2S_3$, Calculated: C, 32.86; H, 2.30; N, 6.39, Found: C, 32.76; H, 2.27; N, 6.43.

EXAMPLE 1

N-[2-[[[5-[(dimethylamino)methyl]2-furanyl]methyl]thio]ethyl]-1,2-benzisothiazol-3-amine 1,1-dioxide To a refluxing solution of 2.14 g (10 mmol) of 2-[[[5-[(dimethylamino)methyl]-2-furanyl]methyl]thio]ethylamine in 150 ml of chloroform is added incrementally 2.02 g (10 mmol) of 3-chlorobenzisothiazole 1,1-dioxide. The reaction mixture is refluxed for an additional 30 minutes, is cooled to room temperature and then solvent is removed on a rotoevaporator. The resulting oil is subjected to preparative column chromatography on silica gel. Elution with methylene chloride followed by methylene chloride: methanol (95:5) yields 420 mg (12%) of a white solid. The solid is suspended in ethyl ether, separated by suction filtration and dried in vacuo to give 270 mg (7%) of the title compound: m.p. 91-94.C.

IR cm$^{-1}$ 3300, 1612, 1585, 1275, 1150, 1119, 775, 748, and 707 cm$^{-1}$; NRM (CDCl$_3$) 2.19 (6H,s), 2.81 (2H,t,J=6 Hz), 3.38 ($\beta$H,s), 3.54 (4H,m), 3.70 (2H,s), 6.08 (1H,d,J=4 Hz), 6.15 (1H,d,J=4 Hz), 7.70 (5H,m), $^{13}$C (CDCl$_3$) 28.50, 30.59, 42.05, 45.02, 55.98, 109.49, 109,92, 121.56, 121.70, 127,89, 132.62, 133.12, 142.62, 150.96, 151.84 and 159.85;

MS m/e 380 (MH+).

EXAMPLE 2

N-[3-[3-[(1-piperidinyl)methyl]phenoxy]propyl]-1,2-benzisothiazol-3-amine 1,1-dioxide To a gently refluxing solution of 3-[3-[(1-piperidinyl)methyl]phenoxy]propylamine (992 mg, 4 mmol) in 90 ml of chloroform is added dropwise a solution of 880 mg (4.4 mmol) of 3-chlorobenzisothiazole 1, 1-dioxide in 30 ml of chloroform. Following the addition, the reaction mixture is refluxed for an additional 15 min., cooled to room temperature and solvent removed in vacuo. Column chromatography of the resultant residue (foam) on silica gel utilizing methylene chloride:methanol:ammonium hydroxide (90:10:1) as eluting solvent affords after evaporation a white solid. The crude product is suspended in ethyl acetate, filtered and dried to give 620 mg (37.5%) of the title compound, m.p., 138°-140° C.

TLC [silica/methanol:ammonium hydroxide (99:1)] Rf 0.33

IR (KBr) 3300, 1612, 1271, 1150, 1118, 770, 746 cm$^{-1}$;

NMR (d$_6$-DMSO) 9.44 [1H (removed by D$_2$O exchange)], 8.13 (1H,m), 7.88 (3H,m), 7.15 (1H,m), 6.79 (3H, broad s), 4.18 (2H,t), 3.65 (2H,t), 3.26 (2H,s), 2.10 (6H,m) and 1.30 (6H, broad s). $^{13}$CNMR (d$_6$-DMSO) 160.06, 159.15, 142.98, 141.12, 134.03, 133.60, 129.71, 128.42, 123.56, 121.71, 115.52, 113.47, 65.72, 63.45, 54.57, 40.53, 28.63, 26.26 and 24.69.

EXAMPLE 3

[4-[[[2-[(1,2-benzisothiazol-3yl)amino]ethyl]thio]methyl]-2-thiazolyl]guanidine S',S'-dioxide To a refluxing solution of 1.3 g (6.6 mmol) of [4-[[[2-[amino]ethyl]thio]methyl]-2-thiazolyl]guanidine in 100 ml of chloroform is added a solution of 1.33 g (6.6 mmol) of 3-chlorobenzisothiazole 1,1-dioxide in 50 ml of chloroform over 20 min. The mixture is maintained at reflux for an additional 30 min. and is then allowed to come to room temperature. Decantation of the chloroform leaves a solid residue which is triturated with methanol and potassium carbonate. The methanol is removed in vacuo and the remaining material is subjected to column chromatography on silica gel. Elution with methylene:chloride methanol:ammonium hydroxide (90:10:1) followed by methylene chloride:methanol:ammonium hydroxide (65:35:1) gives 545 mg (20.8%) of crude product.

Recrystallization from ethanol affords the title compound, m.p. 225°-231° C. (dec.)

IR(KBr) 3440, 3380, 3270, 1615, 1480, 1535, 1450, 1275, 1260, 1145, 1112, 775, 748 and 665 cm$^{-1}$;

NMR (d$_6$-DMSO) 9.51 (1H, broad s [removed by D$_2$O exchange ]), 8.15 (1H,m), 7.85 (3H,m), 6.79 (4H, broad s (removed by D$_2$O exchange)), 6.04 (1H,s), 3.67 (4H,m), 2.76 (2H,t J-6 Hz).

Analysis for: $C_{14}H_{16}N_6O_2S_3$, Calculated: C, 42.40; H, 4.07; N, 21.20, Found: C, 42.25; H, 4.23; N, 20.87.

EXAMPLE 4

3-[[3-[3-[(1-piperidinyl)methyl]phenoxy]propyl]amino]-1H isoindol-1-one, dihydrochloride, quarter hydrate A solution of 248 mg (1 mmol) of 3-[3-[(1-piperidinyl)-methyl]phenoxy]propylamine in 20 ml alcohol-free chloroform is heated to reflux and a solution of 166 mg (1 mmol) of 3-chloro-1H-isoindol-1-one in 20 ml of chloroform is added dropwise over 15 min. The reaction mixture is refluxed for an additional 15 min. cooled to room temperature and solvent removed on a rotoevaporator. The residue is chromatographed on silica gel using methylene chloride:methanol (95:5) followed by methylene chloride:methanol:ammonium hydroxide (95:5:0.5) to yield an oil. Treatment with isopropanolic hydrochloric acid and subsequent crystallization from acetonitrile/ethyl ether and drying in vacuo gives 67 mg (14.7%) of the title compound, m.p. 211°–216° C.

IR (KBr) 3410 (broad), 2745, 2495, 1770, 1643, 1270, 1280, 1040, 719 cm$^{-1}$;

NMR (d$_6$-DMSO) 8.57 (1H,m), 7.87 (3H,m) 7.22 (3H,m), 6.84 (1H,m), 4.12 (6H,m), 3.50 (2H, broad s (removed by D$_2$O exchange)), 3.25 (2H,m), 2.83 (2H,m), 2.09 (2H,m) 1.70 (6H,m).

Analysis for: C$_{23}$H$_{29}$Cl$_2$N$_3$O$_2$·¼H$_2$O Calculated: C, 60.72; H, 6.54; N, 9.24, Found C, 60.77; H, 6.49; N, 9.22.

EXAMPLE 5

N-[3-[3-[(1-piperidinyl)methyl]phenoxy]propyl]-6-nitro-1,2-benzisothiazol-3-amine 1,1-dioxide, hydrochloride To a gently refluxing solution of 496 mg (2 mmol) of 3-[3-[(1-piperidinyl)methyl]phenoxy]propylamine in 25 ml of alumina-treated chloroform is added dropwise over 20 min. 492 mg (2 mmol) of 6-nitropseudosaccharyl chloride (prepared according to the method described in Japanese patent publication 7014302) in 25 ml of chloroform. The mixture is heated for 10 min. following the addition and then is rotoevaporated to an oily foam. Crystallization from absolute ethanol gives crude product which yields 272 mg (27.59) of the title compound upon recrystallization from 95% ethanol: m.p. 223°–227° C., IR (KBr) 1603, 1550, 1318, 1175 cm$^{-1}$.

Analysis for: C$_{22}$H$_{26}$N$_4$O$_5$S·HCl, Calculated: C, 53.37; H, 5.94; N, 11.32, Found: C, 52.93; H, 5.35; N, 11.24.

EXAMPLE 6

N-[3-[3-[(1-piperidinyl)methyl]phenoxy]propyl]-6-amino-1,2-benzisothiazol-3-amine 1,1-dioxide To a solution of 1.98 g (4 mmol) of the compound of Example 5 in 30 ml of ethanol:ammonium hydroxide (5:1) is added 10 ml of an ammonium sulfide solution prepared by dissolving 540 mg (10 mmol) of ammonium chloride and 2.4 g (10 mmol) of sodium sulfide monohydrate in 10 ml of water. The resulting solution is heated to reflux and maintained under a nitrogen atmosphere for 20 min. Removal of the solvent in vacuo is followed by an aqueous sodium bicarbonate:methylene chloride partition. The aqueous phase is subsequently extracted with ethyl acetate and the organic phase dried over magnesium sulfate and evaporated to give 905 mg (52.8%) of the title compound: m.p. 191°–193° C., IR (KBr) 3370, 1612, 1275, 1139 cm$^{-1}$.

Analysis for: C$_{22}$H$_{28}$N$_4$O$_3$S·HCl, Calculated: C, 61.66; H, 6.59; N, 13.07, Found: C, 61.11; H, 6.60; N, 12.81.

EXAMPLE 7

N-[3-[3-[(1-piperidinyl)methyl]phenoxy]propyl]-6-chloro-1,2-benzisothiazol-3-amine 1,1-dioxide, hydrochloride salt hemihydrate To a solution of 248 mg (1 mmol) of 3-[3-[(1-piperidinyl)methyl]phenoxy]propylamine in 10 ml of alcohol-free chloroform is added dropwise a solution of 236 mg (1 mmol) of 6-chloropseudosaccharyl chloride (prepared according to the method described in Japanese patent publication 7014302) in 20 ml of chloroform. The reaction mixture is maintained at reflux for 1 hr, cooled to room temperature, and solvent removed in vacuo. The residue is dissolved in ethanol and treated with ethereal hydrochloric acid. Crystallization of the crude hydrochloride from ethanol gave 128 mg (25.9%) of the title compound: m.p. 210°–215° C.

IR (KBr) 2500, 1642, 1290, 1164 and 1145 cm$^{-1}$.

Analysis for: C$_{22}$H$_{26}$ClN$_3$O$_3$S·HCl·½H$_2$O, Calculated: C, 53,54; H, 5.72; N, 8.51, Found: C, 53.79; H, 5.62; N, 8.33.

EXAMPLE 8

N-[3-[3-[(1-piperidinyl)methyl]phenoxy]propyl]-6-fluoro-1,2-benzisothiazol-3-amine 1,1-dioxide A. 3-chloro-6-fluoro-1,2-benzisothiazole 1,1-dioxide (6-fluoropseudosaccharyl chloride A mixture of 2.0 g (10 mmol) of 6-fluoro-saccharin and 2.1 g (10 mmol) of phosphorus pentachloride in 10 ml of o-dichlorobenzene is heated to reflux and maintained for 1 hr. The reaction mixture is cooled and evaporated to give crude product which is used without characterization.

B.
N-[3-[3-[(1-piperidinyl)methyl]phenoxy]propyl]6-fluoro-1,2-benzisothiazol-3-amine 1,1-dioxide A refluxing solution of 2.0 g (8 mmol) of 3-[3-[(1-piperidinyl)methyl]phenoxy]propylamine is treated dropwise with 2.19 g (10 mmol) of crude 6-fluoropseudosaccharyl chloride. The reaction mixture is maintained at reflux for 10 min. cooled and solvent removed in vacuo. The residual oil is subjected to column chromatography to give after trituration with ethyl ether, and drying the title compound: m.p. 139°–163° C., IR (KBr) 3300, 1642, 1479, 1273, 1145 and 1122 cm$^{-1}$.

Analysis for: C$_{22}$H$_{26}$FN$_3$O$_3$S, Calculated: C, 61.23; H, 6.07; N, 9.73, Found: C, 60.99; H, 6.00; N, 9.34.

EXAMPLE 9

N-[3-[3-[(1-piperidinyl)methyl]phenoxy]propyl]-5,6-dichloro-1,2-benzisothiazol-3-amine 1,1-dioxide, monohydrochloride salt To a refluxing solution of 1.24 g (5 mmol) of 3-[3-[(1-piperidinyl)methyl]phenoxy]propylamine in 30 ml of alumina-treated chloroform is added dropwise 1.35 g (5 mmol) of 5,6-dichloropseudosaccharyl chloride (prepared according to the method described in Japanese patent publication 7014302) in 30 ml of chloroform. The mixture is refluxed for an additional 10 min., cooled to room temperature and solvent removed by rotoevaporation. The resulting foam is crystallized from absolute ethanol and yields upon recrystallization from ethanol:water:tetrahydrofuran, the desired title compound: m.p. 281°–284° C., IR (KBr) 2942, 1628, 1298, 1171 cm$^{-1}$.

Analysis for: C$_{22}$H$_{25}$Cl$_2$H$_3$O$_3$S.HCl, Calculated: C, 50.92; H, 5.05; N, 8.10, Found: C, 50.80; H, 5.17; N, 8.15.

EXAMPLE 10

N-[3-[3-[(1-piperidinyl)methyl]phenoxy]propyl]-5-methyl-1,2-benzisothiazol-3-amine 1,1-dioxide A. 3-chloro-5-methyl-1,2-benzisothiazole 1,1-dioxide A slurry of 5-methyl-1,2-benzisothiazolin-3-one 1,1-dioxide (1.80 g, 9.13 mmoles) and phosphorus pentachloride (2.00 g, 9.59 mmoles) in o-dichlorobenzene (9.0 ml) is heated under dry nitrogen. Complete solution occurs at ca. 85° C. The temperature is raised to 180° C. and maintained at 180° C. for 2 hours. After cooling to room temperature the brown solution is partially evaporated in vacuo at 70° C. to remove the phosphorus oxychloride formed. Addition of pentane and standing overnight at −5° C. gives a gum. Decantation and trituration with three 50 ml portions of hexane gives a gum which cannot be solidified and is used directly in the next step.

B. N-[3-[3-[(1-piperidinyl)methyl]phenoxy]propyl]-5-methyl-1,2-benzisothiazol-3-amine 1,1-dioxide To a refluxing solution of 3-[3-(1-piperidinylmethyl)-phenoxy]propylamine (1.33 g, 5.36 mmoles) in dried chloroform (50 ml) under dry nitrogen is added over 45 minutes a solution of 3-chloro-5-methyl-1,2-benzisothiazole 1,1-dioxide (1.21 g, 5.64 mmoles) in dried chloroform (25 ml) while maintaining reflux. After the addition is complete refluxing is continued for 15 minutes and the clear brown solution is allowed to come to room temperature. Evaporation in vacuo gives a tan solid which cannot be crystallized. Column chromatography on silica gel using methylene chloride/methanol/ammonium hydroxide 95/5/0.5 as eluent gives the free methanol base as a brown foam, 1.22 g. Trituration with ether gives an off-white colored solid, 0.73 g, m.p. 120°-124° C. Recrystallization from ethyl acetate/pentane and finally ethyl acetate gives the pure product, 0.169 tan solid, m.p. 120°-4° C. IR (KBr) 3300, 2938, 1622, 1530 cm$^{-1}$; NMR (in DMSO) 6.8-8.0 (7H,m), 4.05 (2H,t), 3.76 (2H,t), 1.37 (6H,s), 1.4 (6H,s), 2.0-2.4 (6H,m), 2.5 (3H,s), 3.4 (2H,s), 3.6 (2H,t), 4.1 (2H,t), 6.7-8.0 (7H,m), 9.3 (1H,n).

Analysis for: C$_2$H$_{29}$N$_3$O$_3$S, Calculated: C, 64.61; H, 6.84; N, 9.87, Found: C, 64.25; H, 6.84; N, 9.56.

EXAMPLE 11

N-[3-[3-[(1-piperidinyl)methyl]phenoxy]propyl]-5-chloro-1,2-benzisothiazol-3-amine 1,1-dioxide, hydrochloride A. 3,5-dichloro-1,2-benzisothiazole 1,1-dioxide A slurry of 5-chloro-1,2-benzisothiazolin-3-one 1,1-dioxide (1.50 g, 6.89 mmoles), and phosphorus pentachloride (1.51 g, 7.24 mmoles) in o-dichlorobenzene (25 ml) is heated under dry nitrogen. At 80° C. hydrogen chloride evolution appears to start. At ca. 90° C. complete solution occurs. The temperature is raised and maintained at 180°-185° C. for 2 hours. After cooling to room temperature the tan solution is partially stripped in vacuo at 70° C. to remove the phosphorus oxychloride formed. Addition of pentane (100 ml) to the cooled residue gives a tan solid, 0.767 g, m.p. 130°-136° C., IR (KBr) 1528, 1344, 1173 cm$^{-1}$; NMR (in DMSO) 7.47-8.28 (m).

B. N-[3-[3-[(1-piperidinyl)methyl]phenoxy]propyl]-5-chloro-1,2-benzisothiazol-3-amine 1,1-dioxide, hydrochloride To a refluxing solution of 3-[3-(1-piperidinylmethyl)-phenoxy]propylamine (0.700 g, 2.82 mmoles) in dried chloroform (30 ml) under dry nitrogen is added over 45 minutes a solution of 3,5-dichloro-1,2-benzisothiazole 1,1-dioxide (0.699 g, 2.96 m moles) in dried chloroform (15 ml) while maintaining reflux. After the addition is complete, refluxing is continued for 15 minutes and the clear tan solution allowed to come to room temperature. Evaporation in vacuo gives a yellow-orange foam. Crystallization from methylene chloride/acetonitrile gives a yellow solid, 1.034 g, m.p. 242°-245° C. Recrystallization from ethanol gives a yellow solid, 0.257 g, m.p. 242°-244° C.

IR (KBr) 2950, 2540, 1620; NMR (in DMSO) 1.8 (6H,s), 2.2 (2H,t), 2.9 (2H,n), 3.3 (2H,n), 3.7 (2H,n), 4.2 (4H,n); 6.9-815 (7H,n), 9.9 (1Hn); 10.1 (1H,m).

Analysis for: C$_{22}$H$_{26}$ClN$_3$O$_3$S.HCl, Calculated: C, 54.55; H, 5.62; N, 8.67; Cl, 14.64, Found: C, 54.54; H, 5.61; N, 8.82; Cl, 14.92.

EXAMPLE 12

N-[3-[3-[(1-piperidinyl)methyl]phenoxy]propyl]-5-methoxy-1,2-benzisothiazol-3-amine 1,1-dioxide, 2/3 oxalate, ethanolate A. 3-chloro-5-methoxy-1,2-benzisothiazole 1,1-dioxide A slurry of 5-methoxy-1,2-benzisothiazolin-3-one 1,1-dioxide (1.60 g, 7.504 mmoles) and phosphorus pentachloride (1.64 g, 7.879 mmoles) in o-dichlorobenzene (9.0 ml) is heated under dry nitrogen. At 100° C. hydrogen chloride evolution appears to start and complete solution also occurs. The temperature is raised to 180° C. and maintained at 180° C. for 2 hours. After cooling to room temperature the solution is partially evaporated in vacuo at 70° C. to remove the phosphorus oxychloride formed. Addition of pentane (50 ml), and stirring overnight at room temperture gives a tan gum. Decantation and trituration with three 50 ml portions of pentane gives on filtering a light tan solid, m.p. 50°-85° C.

IR (KBr) 1725 (shoulder) 1297, 1340, 1175, NMR (in DMSO) 3.9 (s, starting material), 4.0 (s), 7.2-8.2 (aromatic), 12.7 (s, starting material).

B. N-[3-[3-[(1-piperidinyl)methyl]phenoxy]propyl]-5-methoxy-1,2-benzisothiazol-3-amine 1,1-dioxide 2/3 oxalate, ethanolate To a refluxing solution of 3-[3-(1-piperidinylmethyl)-phenoxy]propylamine (1.33 g, 5.355 mmoles) in dried chloroform (50 ml) under dry nitrogen is added over 45 minutes a solution of 3-chloro-5-methoxy-1,2-benzisothiazole 1, 1-dioxide (1.30 g, 5.623 mmoles) in dried chloroform (25 ml) while maintaining reflux. After the addition is complete, refluxing is continued for 45 minutes and the solution allowed to come to room temperature. Evaporation in vacuo gives a sticky residue which cannot be crystallized. Column chromatography on silica gel using 95/5/0.5 methylene chloride/methanol/ammonium hydroxide as eluent gives the free base has a tan foam 1.703 g which cannot be crystallized. Treatment with anhydrous oxalic acid in ethanol gives the title compound, 0.302 g, tan solid, m.p. 114°–120° C. (from 0) and clear by 240° C.

IR (KBr) 2960, 1620, 1338, 1170 cm$^{-1}$ NMR (In DMSO) 1.5 (6H,s), 2.2 (2H,t), 2.7 (4H,s), 3.6 (2H,t), 3.9 (3H,s and 2H,s), 4.1 (2H,t) 6.9–7.9 (7H,m), 9.5 (1H,s). Also one mole EtOH.

Analysis for: $C_{23}H_{29}N_3O_3S.2/3CO_2H\ C_2H_5\ OH\ CO_2H$, Calculated: C, 57.54; H, 6.66; N, 7.64, Found: C, 57.30; H, 6.73; N, 7.71.

EXAMPLE 13

N-[3-[3-[(1-piperidinyl)methyl]phenoxy]propyl]-6-sulfamoylbenzisothiazol-3-amine 1,1-dioxide A. 6-sulfamoyl-benzisothiazolin-3-thione 1,1-dioxide To a mixture of 5.25 g (20 mmol) of 6-sulfamoyl-saccharin in 50 ml of diglyme is added 13.4 g (30 mmol) of phosphorus pentasulfide and 6.75 g (80 mmol) of sodium bicarbonate. The mixture is allowed to stand at room temperature for 30 min. and then is heated to 70° C. for 2 hours.

The reaction mixture is diluted with water and is extracted with methylene chloride and ethyl ether sequentially. The aqueous phase is acidified with dilute aqueous hydrochloric acid and reextracted with methylene chloride and ethyl ether. All the organic extracts are dried over magnesium sulfate, rotoevaporated and placed under high vacuum. The resulting orange solid is triturated with benzene, filtered and dried overnight to give the title compound: m.p. 250°–252° C. (dec.); IR (KBr) 3350, 3275, 1335, 1178, 1156 and 845 cm$^{-1}$.

Analysis for: $C_7H_6N_2O_4S_3$, Calculated: C, 30.20; H, 2.17; N, 10.07, Found: C, 34.64; H, 3.64; N, 8.01.

B. 6-sulfamoyl-3-thiomethyl benzisothiazole 1,1-dioxide

To a solution of 2.8 g (10 mmol) of A. above in 10 ml of dimethylformamide is added 937 ml (15 mmol) of iodomethane. The reaction mixture is allowed to stand at room temperature for 40 minutes and then is partitioned between aqueous sodium bicarbonate and methylene chloride. A precipitate is observed, separated by filtration, and extracted with ethyl acetate to give 297 mg of the title compound.

The aqueous phase is then extracted with ethyl acetate to give, after combination with the methylene chloride extract, drying over magnesium sulfate and rotoevaporation, 285 mg of alkylated product: m.p. 280°–282° C., IR (KBr) 3365, 3230, 1489, 1332, 1320, 1160 and 825 cm$^{-1}$.

Analysis for: $C_8H_8N_2O_4S_3$, Calculated: C, 32.86; H, 2.76; N, 9.58, Found: C, 34.67; H, 3.06; N, 9.91.

C. N-[3-[3-[(1-piperidinyl)methyl]phenoxy]propyl]-6-sulfamoyl-1,2-benzisothiazol-3-amine 1,1-dioxide To a gently refluxing solution of 372 mg (1.5 mmol) of 3-[3-[(1-piperidinyl)methyl]phenoxy]propylamine in 50 ml of alumina-treated chloroform is added a suspension of 3-thiomethyl-6-sulfamoyl benzisothiazole 1,1-dioxide (438 mg, 1.5 mmol) in 50 ml of chloroform-:acetonitrile (1:1).

The reaction mixture is maintained at reflux for 1 hr, cooled to room temperature and solvent removed in vacuo. The residue is triturated with isopropyl ether and the resulting yellow solid filtered and dried (100° C., high vacuum) to give 482 mg of title adduct: m.p. 155°–159° C., IR (KBr), 1612, 1280, 1140 and 822 cm$^{-1}$.

Analysis for: $C_{22}H_{28}N_4O_5S_2$, Calculated: C, 53.64; H, 5.73; N, 11.39, Found: C, 52.96; H, 5.71; N, 11.02.

EXAMPLE 14

N-[3-[3-[(1-piperidinyl)methyl]phenoxy]propyl]-6-bromo-1,2-benzisothiazol-3-amine 1,1-dioxide, hydrochloride A mixture of 4.00 g (15 mmol) 6-bromo-1,2-benzisothiazol-3(2H)-one 1,1-dioxide and 3.57 g (17 mmol) phosphorus pentachloride in 5 ml o-dichlorobenzene is heated from ambient temperature to 160° C. over one hour and is held at that temperature for one additional hour. Upon cooling, liquids are removed in vacuo and the residual 6-bromo-3-chlorobenzisothiazole 1,1-dioxide is suspended in acetonitrile and added portionwise to a solution of 3.7 g (15 mmol) 3-[3-[(1-piperidinyl)methyl]phenoxy]propylamine in refluxing acetonitrile. Heating at reflux is continued for one hour after completion of the addition, after which the reaction mixture is cooled to room temperature. The solution is decanted away from a small quantity of gum and the solvent is removed on a rotoevaporator. The resulting oil is dissolved in absolute ethanol, from which the title compound precipitates. m.p. 217°–220° C. IR (KBr) 1625, 1290, 1165, 1150 cm$^{-1}$ Analysis for: $C_{22}H_{27}BrClN_3O_3S$, Calculated: C, 49.96; H, 5.15; N, 7.94, Found: C, 49.76; H, 5.21; N, 7.46.

EXAMPLE 15

N-[3-[3-[(1-piperidinyl)methyl]phenoxy]propyl]-5-fluoro-1,2-benzisothiazol-3-amine 1,1-dioxide, hydrochloride A. 3-chloro-5-fluoro-1,2-benzisothiazole 1,1-dioxide A slurry of 5-fluoro-1,2-benzisothiazolin-3-one 1,1-dioxide (1.80 g, 8.948 mmoles) and phosphorus pentachloride (1.96 g, 9.412 mmoles) in o-dichlorobenzene (9.0 ml) is heated under dry nitrogen. At 70° C. hydrogen chloride evolution appears to start. At ca. 105° C. complete solution occurs. The temperature is raised and maintained at 175°–185° C. for 2½ hours. After cooling to room temperature the solution is partially stripped at 70° C. in vacuo to remove the phosphorus oxychloride formed. Addition of pentane (80 ml) with stirring gives a light tan solid, 0.91 g, m.p. 142°–147°, IR (KBr) 1548, 1351, 1170 cm$^{-1}$; NMR (in DMSO) 7.74–8.53(m).

B. N-[3-[3-[(1-piperidinyl)methyl]phenoxy]propyl]-5-fluoro-1,2-benzisothiazol-3-amine 1,1-dioxide, hydrochloride To a refluxing solution of 3-[3-(1-piperidinylmethyl)-phenoxy]propylamine (0.870 g, 3.503 mmoles) in dried chloroform (35 ml) under dry nitrogen is added over 45 minutes a solution of 3-chloro-5-fluoro-1,2-benzisothiazole 1,1-dioxide (0.808 g, 3.679 mmoles) in dried chloroform (20 ml) while maintaining reflux. After the addition is complete refluxing is continued for 15 minutes and the solution allowed to come to room temperature. Evaporation in vacuo gives an orange solid. Recrystallization from isopropanol gives a light tan solid. m.p. 224°–226° after softening from 200° C. IR (KBr) 2950, 1600, 1302, 1171 cm$^{-1}$; NMR (in DMSO) 1.76 (6H,s), 2.2 (2H,t), 2.8 (2H,m), 3.3 (3H,m), 3.6 (2H,t), 4.2 (3Hm,), 7.0–8.5 (7H,m), 10.1 (1h,s), 10.6 (1H,m).

Analysis for: $C_{22}H_{26}FN_3O_3S \cdot HCl$, Calculated: C, 56.46; H, 5.81; N, 8.98; Cl, 7.58, Found: C, 56.26; H, 5.87; N, 9.04; Cl, 7.50.

EXAMPLE 16

N-[3-[3-(4-morpholinylmethyl)phenoxy]propyl]-1,2-benzisothiazol-3-amine 1,1-dioxide, hydrochloride

A. 3-(4-morpholinylmethyl)phenol

To a solution of 15 g. (0.123 mole) of 3-hydroxybenzaldehyde in 150 ml of ethanol is added 26.5 g (0.304 mole) of morpholine. Then 4.7 g (0.124 mole) of sodium borohydride is added portionwise over 1 hour. The solution is stirred for 1 hour and allowed to sit overnight. The solvent is then evaporated via a rotary evaporator and the residue triturated with 200 ml cold water. After acidification with concentrated HCl, the solution is extracted with ethyl acetate. The aqueous layer is basified with ammonium hydroxide and extracted again with 100 ml ethyl acetate. The organic layer is dried over $MgSO_4$, filtered and evaporated. The residue is recrystallized twice from acetonitrile to give 6.3 g of product m.p. 113°-15° C.

Analysis for: $C_{11}H_{15}NO_2$, Calculated: C, 68.37; H, 7.82; N, 7.25, Found: C, 68.17; H, 7.73; N, 7.35.

B. 2-[3-[3-(4morpholinylmethyl)phenoxy]propyl]-1H-isoindole-1,3(2H)-dione

To 1.58 g (0.033 moles) of 50% sodium hydride is added 15 ml DMF; then 6.3 g (0.033 moles) of 3-(4-morpholinylmethyl)phenol, dissolved in 30 ml DMB, is added dropwise to the stirred suspension at room temperature. This mixture is stirred 20 minutes and then N-(3-bromopropyl)-phthalimide, 9 g. (0.033 moles) is added to the mixture and stirred. A clear, amber solution results. After 2 hours, this solution is poured into ice-water and extracted with 100 ml of chloroform. The organic layer is washed once with 100 ml 5%NaOH, and once with 100 ml water, dried over $MgSO_4$, filtered and evaporated. The residue is dissolved in ether and washed again with 50 ml water. Then the organic layer is dried over $MgSO_4$, filtered and evaporated. The residue rapidly forms a white solid. This is recrystallized from acetonitrile, m.p. 90°-93° C. (yield=39 g).

Analysis for: $C_{22}H_{24}N_2O_4$, Calculated: C, 69.45; H, 6.36; N, 7.37, Found: C, 69.07; H, 6.45; N, 7.21.

C. 3-[3-(4-morpholinylmethyl)phenoxy]-1-propanamine

A solution of 4.35 g (0.011 moles) of 2-[3-[3-(4-morpholinylmethyl)phenoxy]propyl]-1H-isoindole-1,2(2H)-dione in 85 ml of ethanol is added to 7 ml (0.14 moles) of hydrazine hydrate and stirred at room temperature for 2 hours. The precipitate is filtered off and the filtrate evaporated to dryness. Benzene is added and distilled off to azeotrope water. Then chloroform is added and the precipitate formed is filtered off. The filtrate is dried over $MgSO_4$, filtered and evaporated, leaving 1.7 g of low viscosity, yellow-liquid. This crude product is used without further purification.

D. N-[3-[3-(4-morpholinylmethyl)phenoxy]propyl]-1,2-benzisothiazol-3-amine 1,1-dioxide hydrochloride A solution of 1.37 g (0.0068 moles) of 3-chlorobenzoisothiazole 1,1-dioxide is added dropwise to 1.7 g (0.0068 moles) of 3-[3-(4-morpholinylmethyl)phenoxy]-1-propanamine in 150 ml of gently refluxing chloroform, over 30 minutes. The reflux is continued for 15 minutes after the end of the addition, then the reaction mixture is evaporated to dryness. The residue is treated with ethanol-ethyl acetate, causing the formation of a yellow-white solid. m.p. 21° C. (dec.) Recrystallization of the crude product from ethanol gave a m.p. of 215° C. (dec.) (1.7 g yield).

Analysis for: $C_{21}H_{26}ClN_3O_4$, Calculated: C, 55.80; H, 5.80; N, 9.30, Found: C, 55.98; H, 6.03; N, 9.55.

EXAMPLE 17

Preparation of Amines

Following the procedures of Example 16A-C, there are prepared the following intermediate amines:

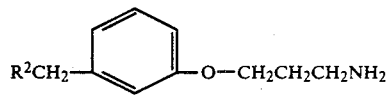

(1) 3-(3-aminopropoxy)-N,N-dipropylbenzenemethanamine, dihydrochloride.
$R^2H$:dipropylamine
Melting point of amine: 200° C. (dec.)
Analysis for: $C_{16}H_{30}Cl_2N_2O$, Calculated: C, 56.97; H, 8.97; N, 8.31, Found: C, 56.78; H, 8.67; N, 8.26.

(2) 3-(3-aminopropoxy)-N,N-diethylbenzenemethanamine hydrochloride
$R^2H$:diethylamine
Melting point of amine: 147° C. (dec.)
Analysis for: $C_{14}H_{26}Cl_2N_2O$, Calculated: C, 54.37; H, 8.47; N, 9.06, Found: C, 54.58; H, 8.29; N, 8.93.

(3) 3-[3-(1-pyrrolidinylmethyl)phenoxyl]-1-propanamine $R^2H$:pyrrolidine
Melting point of amine:product is an oil (4) 3-(3-aminopropoxy)-N,N-dimethylbenzenemethanamine, dihydrochloride
$R^2H$:dimethylamine
Melting point of amine:208°-10° C.
Analysis for: $C_{12}H_{22}Cl_2N_2O$, Calculated: C, 51.25; H, 7.89; N, 9.96, Found: C, 51.57; H, 7.75; N, 9.91.

(5) 3-(3-aminopropoxy)-N,N-dibutylbenzenemethanamine $R^2H$:n-dibutylamine
Melting point of amine:product is an oil.

(6) 3-[3-(4-thiomorpholinylmethyl)phenoxy]-1-propanamine $R^2H$:thiomorpholine (7) 3-[3-(hexahydro-1H-azepin-1-ylmethyl)phenoxy]-1-propanamine
$R^2H$:hexamethyleneimine
Analysis for: $C_{16}H_{26}N_2O$, Calculated: C, 73.25; H, 9.99; N, 10.68, Found: C, 73.04; H, 10.12; N, 10.27.

(8) 3-[3-(3-thiazolidinylmethyl)phenoxy]-1-propanamine, dihydrochloride hemihydrate
$R^2H$:thiazolidine
Melting point of amine:salt has m.p. of 160°-5° C. free base is an oil
Analysis for: $C_{13}H_{22}Cl_2N_2OS \cdot \frac{1}{2}H_2O$, Calculated: C, 46.70; H, 6.93; N, 8.38, Found: C, 46.92; H, 6.37; N, 8.07.

(9) 3-[3-[(octahydro-1(2H)-azocinyl)methyl]phenoxy]-1-propanamine
$R^2H$:heptamethyleneimine

(10) 3-(3-aminopropoxy)-N-cyclohexylbenzenemethanamine, dihydrochloride
$R^2H$:cyclohexylamine
Melting point of amine:salt has m.p. of 183°-7° C.

(11) 3-(3-aminopropoxy)-N-cyclopentylbenzenemethanamine, dihydrochloride

R²H:cyclopentylamine
Melting point of amine:salt has m.p. of 183°–5° C.
Analysis for: $C_{15}H_{26}Cl_2N_2O$, Calcualted: C, 56.07; H, 8.16; N, 8.72, Found: C, 56.03; H, 8.04; N, 8.63.

(12) N-[[3-(3-aminopropoxy)phenyl]methyl]-2-furanmethanamine, dihydrochloride
R²H:furfurylamine
Melting point of amine:salt has m.p. of 238°–40° C.
Analysis for: $C_{15}H_{22}Cl_2N_2O_2$, Calculated: C, 54.06; H, 6.66; N, 8.41, Found: C, 53.88; H, 6.55; N, 8.46.

(13) 3-(3-aminopropoxy)-N-(phenylmethyl)benzenemethanamine, dihydrochloride
R²H:benzylamine
Melting point of amine:salt has m.p. of 248°–50° C.
Analysis for: $C_{17}H_{24}Cl_2N_2O$, Calculated: C, 59.47; H, 7.05; N, 8.16, Found: C, 59.13; H, 6.90; N, 8.16.

(14) 3-(3-aminopropoxy)-N,N-bis(2-methylpropyl)-benzenemethanamine
R²H:diisobutylamine
Melting point of amine:product is an oil

(15) 3-(3-aminopropoxy)-N-butylbenzenemethanamine, dihydrochloride
R²H:n-butylamine
Melting point of amine:salt has m.p. of 235°–9° C.
Analysis for: $C_{14}H_{26}Cl_2N_2O$, Calculated: C, 54.37; H, 8.47; N, 9.06, Found: C, 54.26; H, 8,34; N, 9.02.

(16) 3-(3-aminopropoxy)-N-phenylaminobenzenemethanamine, dihydrochloride
R²H:aniline
Melting point of amine:salt has m.p. of 157°–60° C.
Analysis for: $C_{16}H_{22}N_2Cl_2O$, Calculated: C, 55.36; H, 6.74; N, 8.51, Found: C, 58.11; H, 6.62; N, 8.40.

(17) 3-(3-aminopropoxy)-N-methylpentylbenzenemethanamine
R²H:N-methyl-N-amylamine
Melting point of amine:product is an oil

(18) 3-(3-aminopropoxy)-N-butyl-N-propylbenzenemethanamine
R²H:n-butyl-n-propylamine
Melting point of amine:product is an oil

(19) 3-(3-aminopropoxy)-N-butyl-N-methylbenzenemethanamine
R²H:N-methyl-n-butylamine
Melting point of amine:product is an oil
Analysis for: $C_{15}H_{26}N_2O$, Calculated: C, 71.95; H, 10.47; N, 11.19, Found: C, 71.53; H, 10.22; N, 10.55.

(20) 3-(3-aminopropoxy)-N,N,-dipentylbenzenemethanamine R²H:N,N-diamylamine
Melting point of amine:product is an oil
Analysis for: $C_{20}H_{36}N_2O$, Calculated: C, 74.95; H, 11.32; N, 8.74, Found: C, 74.97; H, 10.81; N, 8.49.

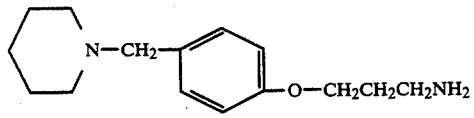

(21) 3-[4-(1-piperidinylmethyl)phenoxy]-1-propanamine
Starting materials:piperidine and 4-hydroxybenzaldehyde
Melting point of amine:product is an oil
Analysis for: $C_{15}H_{24}N_2O$, Calculated: C, 72.54; H, 9.74; N, 11.28, Found: C, 72.31; H, 9.78; N, 11.72.

EXAMPLES 18–38

Following the procedure of Example 16D., there are prepared the following final products:

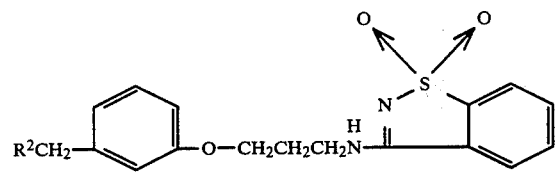

18. N-[3-[3-[(dipropylamino)methyl]phenoxy]propyl]-1,2-benzisothiazol-3-amine 1,1-dioxide, hydrochloride
Starting amine: Example 17(1)
Melting point: 205°–8° C. (dec.)
Analysis for: $C_{23}H_{32}N_3O_3SCl$, Calculated: C, 59.27; H, 6.92; N, 9.02, Found: C, 59.38; H, 6.96; N, 8.87.

19. N-[3-[3-[(diethylamino)methyl]phenoxy]propyl]-1,2-benzisothiazol-3-amine 1,1-dioxide, hydrochloride
Starting amine: Example 17(2)
Melting point: 184°–7° C. (dec.)
Analysis for: $C_{21}H_{28}ClN_3O_3S$, Calculated: C, 57.59; H, 6.44; N, 9.60, Found: C, 57.74; H, 6.54; N, 9.39.

20. N-[3-[3-(1-pyrrolidinylmethyl)phenoxy]propyl]-1,2-benzisothiazol-3-amine 1,1-dioxide, hydrochloride, ½ hydrate
Starting amine: Example 17(3)
Melting point: 193°14 5° C.
Analysis for: $C_{21}H_{25}N_3O_3S \cdot HCl \cdot \frac{1}{2}H_2O$, Calculated: C, 57.07; H, 6.06; N, 9.50, Found: C, 57.14; H, 5.97; N, 9.49.

21. N-[3-[3-[(dimethylamino)methyl]phenoxy]propyl]-1,2-benzisothiazol-3-amine 1,1-dioxide, hydrochloride, hemihydrate
Starting amine: Example 17(4)
Melting point: 188°–92° C. (dec.)
Analysis for: $C_{19}H_{24}ClN_3O_3S \cdot \frac{1}{2}H_2O$, Calculated: C, 54.47; H, 6.02; N, 10.03, Found: C, 54.32; H, 5.71; N, 10.17.

22. N-[3-[3-[(dibutylamino)methyl]phenoxy]propyl]-1,2-benzisothiazol-3-amine 1,1-dioxide, hydrochloride, hemihydrate
Starting amine: Example 17(5)
Melting point: 157° C. (dec.)
Analysis for: $C_{25}H_{36}ClN_3O_3S \cdot \frac{1}{2}H_2O$, Calculated: C, 59.68; H, 7.41; N, 8.35, Found: C, 59.57; H, 7.16; N, 8.42.

23. N-[3-[3-[(4-thiomorpholinyl)methyl]phenoxy]propyl]-1,2-benzisothiazol-3-amine 1,1-dioxide, hydrochloride
Starting amine: Example 17(6)
Melting point: 208°–12° C.
Analysis for: $C_{21}H_{26}ClN_3O_3S_2$, Calculated: C, 53.89; H, 5.60; N, 8.98, Found: C, 53.93; H, 5.69; N, 8.78.

24. N-[3-[3-[(hexahydro-1H-azepin-1-yl)methyl]phenoxy]-propyl]-1,2-benzisothiazol-3-amine 1,1-dioxide, hydrochloride
Starting amine: Example 17(7)
Melting point: 190°–2° C.
Analysis for: $C_{23}H_{29}N_3O_3S \cdot HCl$, Calculated: C, 59.52; H, 6.52; N, 9.06, Found: C, 59.11; H, 6.70; N, 8.84.

25. N-[3-[3-[(3-thiazolidinyl)methyl]phenoxy]propyl]-1,2-benzisothiazol-3-amine 1,1-dioxide, hydrochloride
Starting amine: Example 17(8)
Melting point: 162°–6° C.

Analysis for: $C_{20}H_{24}ClN_3O_3S_2$, Calculated: C, 52.91; H, 5.33; N, 9.26, Found: C, 52.91; H, 5.22; N, 9.10.

26. N-[3-[3-[(octahydro-1(2H)-azocinyl)methyl]phenoxy]-propyl]-1,2-benzisothiazol-3-amine 1,1-dioxide, hydrochloride Starting amine: Example 17(9)
Melting point: 163°–5° C.
Analysis for: $C_{24}H_{32}ClN_3O_3S$, Calculated: C, 60.30; H, 6.75; N, 8.79, Found: C, 60.03; H, 6.86; N, 8.74.

27. N-[3-[3-[(cyclohexylamino)methyl]phenoxy]propyl]-1,2-benzisothiazol-3-amine 1,1-dioxide, hydrochloride Starting amine: Example 17(10)
Melting point: 198°–203° C.
Analysis for: $C_{23}H_{30}ClN_3O_3S$, Calculated: C, 59.63; H, 6.52; N, 9.06, Found: C, 59.42; H, 6.63; N, 8.97.

28. N-[3-[3-[(cyclopentylamino)methyl]phenoxy]-propyl]-1,2-benzisothiazol-3-amine 1,1-dioxide, hydrochloride Starting amine: Example 17(11)
Melting point: 198°–201° C.
Analysis for: $C_{22}H_{28}ClN_3O_3S$, Calculated: C, 58.82; H, 6.27; N, 9.34, Found: C, 58.77; H, 6.46; N, 9.08.

29. N-[3-[3-[[(2-furanyl)methyl]amino]methyl]phenoxy]-propyl]-1,2-benzisothiazol-3amine 1,1-dioxide, hydrochloride Starting amine: Example 17(12)
Melting point: 169°–71° C.
Analysis for: $C_{22}H_{24}ClN_3O_4S$, Calculated: C, 57.20; H, 5.24; N, 9.10, Found: C, 57.02; H, 5.29; N, 8.99.

30. N-[3-[3-[(benzylamino)methyl]phenoxy]propyl]-1,2-benzisothiazol-3-amine 1,1-dioxide, hydrochloride, quarter hydrate Starting amine: Example 17(13)
Melting point: 119° C. (dec.)
Analysis for: $C_{24}H_{26}ClN_3O_3S\cdot\frac{1}{4}H_2O$, Calculated: C, 60.49; H, 5.61; N, 8.82, Found: C, 60.38; H, 5.61; N, 8.54.

31. N-[3-[3-[[bis(2-methylpropyl)amino]methyl]phenoxy]-propyl]-1,2-benzisothiazol-3-amine 1,1-dioxide Starting amine: Example 17(14)
Melting point: 141°–3° C.
Analysis for: $C_{25}H_{35}N_3O_3S$, Calculated: C, 65.61; H, 7.71; N, 9.18, Found: C, 65.39; H, 7.63; N, 9.16.

32. N-[3-[3-[(butylamino)methyl]phenoxy]propyl]-1,2-benzisothiazol-3-amine 1,1-dioxide, hydrochloride, hemihydrate Starting amine: Example 17(15)
Melting point: 95°–100° C.
Analysis for: $C_{21}H_{28}ClN_3O_3S\cdot\frac{1}{2}H_2O$, Calculated: C, 56.43; H, 6.54; N, 9.40, Found: C, 56.47; H, 6.42; N, 9.19.

33. N-[3-[3-[(phenylamino)methyl]phenoxy]propyl]-1,2-benzisothiazol-3-amine 1,1-dioxide Starting amine: Example 17(16)
Melting point: 177°–80° C.
Analysis for: $C_{23}H_{23}N_3O_3S$, Calculated: C, 65.54; H, 5.50; N, 9.97, Found: C, 65.40; H, 5.59; N, 9.94.

34. N-[3-[3-[(methylpentylamino)methyl]phenoxy]propyl]-1,2-benzisothiazol-3-amine 1,1-dioxide Starting amine: Example 17(17)
Melting point: 113°–15° C.
Analysis for: $C_{23}H_{31}N_3O_3S$, Calculated: C, 64.31; H, 7.27; N, 9.78, Found: C, 64.17; H, 7.24; N, 9.51.

35. N-[3-[3-[(butylpropylamino)methyl]phenoxy]-propyl]-1,2-benzisothiazol-3-amine 1,1-dioxide Starting amine: Example 17(18)
Melting point: 124°–8° C.
Analysis for: $C_{24}H_{33}N_3O_3S$, Calculated: C, 64.98; H, 7.50; N, 9.47, Found: C, 65.21; H, 7.42; N, 9.70.

36. N-[3-[3-[(butylmethylamino)methyl]phenoxy]-propyl]-1,2-benzisothiazol-3-amine 1,1-dioxide Starting amine: Example 17(19)
Melting point: 114°–6° C.
Analysis for: $C_{22}H_{29}N_3O_3S$, Calculated: C, 63.58; H, 7.03; N, 10.11, Found: C, 63.60; H, 7.12; N, 10.10.

37. N-[3-[3-[(dipentylamino)methyl]phenoxy]-propyl]-1,2-benzisothiazol-3-amine 1,1-dioxide Starting amine: Example 17(20)
Melting point: 109°–11° C.
Analysis for: $C_{27}H_{39}N_3O_3S$, Calculated: C, 66.77; H, 8.09; N, 8.65, Found: C, 66.44; H, 8.07; N, 8.41.

38. N-[3-[4-[(1-piperidinyl)methyl]phenoxy]propyl]-1,2-benzisothiazol-3-amine 1,1-dioxide, hydrochloride Starting amine: Example 17(21)
Melting point: 211°–3° C.
Analysis for: $C_{22}H_{27}N_3O_3S\cdot HCl$, Calculated: C, 58.72; H, 6.27; N, 9.34, Found: C, 58.66; H, 6.33; N, 9.33.

EXAMPLE 39

N-[2-[[[5-[(Dimethylamino)Methyl]-2-Furanyl]Methyl]Thio]Ethyl]Thieno[3,4-d]Isothiazol-3-Amine-1,1-Dioxide To a suspension of 1.8 g. (0.0082 m.) of 3-(methylthio)thieno[3,4-d]isothiazole-1,1-dioxide in 10 ml. of ethanol is added 1.76 g. (0.0082 m.) of 2-[[[5-[(dimethylamino)methyl]-2-furanyl]methyl]thio]ethylamine with stirring at room temperature. The reaction mixture is heated to reflux and heating is continued for 1.5 hours. At this time the reaction mixture is filtered to remove insoluble material and then evaporated to dryness. The product is purified using a silica gel column with methanol as the eluant. The desired fraction was evaporated to dryness and then triturated with ether to give 120 mg. a white solid with a m.p. 100°–103° C.

Analysis for: $C_{15}H_{19}N_3O_3S_3$, Calculated: C, 46.19; H, 5.02; N, 10.77, Found: C, 46.05; H, 4.87; N, 11.04.

EXAMPLE 40

[4-[[[2-[(Thieno[3,4-d]Isothiazol-3-yl)Amino]Ethyl]Thio]Methyl]-2-Thiazolyl]Guanidine-S',S'-Dioxide A mixture of 0.5 g. (0.0022 mole) of [4-[[(2-aminoethyl)thio]methyl]-2-thiazolyl]guanidine and 0.48 (0.0022 mole) of 3-(methylthio)thieno[3,4-d]isothiazole-1,1-dioxide is slowly heated in an oil bath. After the temperature of the oil bath reaches 130° C., the heating is terminated. When the temperature of the oil bath reaches 90° C., 25 ml. of ethanol is added to the mixture. The mixture is then heated under reflux for 30 minutes, and then filtered. The filtrate, on standing, deposits a second crop, which is combined with the original filter cake. This combined filtered cake is dissolved in 300 ml. of boiling ethanol. The solution is cooled to room temperature and diluted with petroleum ether to the cloudy point (about 500 ml.). The mixture is cooled in ice to precipitate 0.5 g. of product, m.p. 223°–5° (dec.).

Analysis for: $C_{12}H_{14}N_6O_2S_4$, Calculated: C, 35.80; H, 3.51; N, 20.88, Found: C, 35.82; H, 3.68; N, 20.45.

EXAMPLE 41

N-[2-[3-(1-Piperidinylmethyl)Phenoxy]Propyl]-Thieno[3,4-d]Isothiazol-3-Amine, 1,1-Dioxide To a solution of 8.3 g. (0.038 moles) of 3-(methylthiothieno[3,4-d]isothiazole-1,1-dioxide in 20 ml. of ethanol is added 9.4 g. (0.038 moles) of 3-[3-[(1-piperidinyl)methyl]phenoxyl]propylamine in 20 ml. of ethanol and this mixture is heated at reflux for 2 hours. Upon cooling, the product precipitates out and the crude material is then recrystallized from ethyl acetate (and treated with charcoal at the same time) to give an 8.0 g. yield of product having a m.p. 145°-7° C.

Analysis for: $C_{20}H_{25}N_3O_3S_2$, Calculated: C, 57.25; H, 6.01; N, 10.02, Found: C, 57.55; H, 6.18; N, 9.94.

EXAMPLE 42

The guinea pig heart atrium test is carried out as follows:

A guinea pig right atrium is suspended at 1 g. tension (isometric) in a thermostatically controlled (32° C.) tissue bath (10 ml) containing oxygenated (95% $O_2$; 5% $CO_2$) Krebs-Haenseleit buffer (pH 7.4). The tissue is allowed to stabilize over 1 hour. Individual contractions are recorded with a force-displacement transducer through a strain gauge coupler. A control dose-response curve to histamine in the above described tissue bath is obtained after which the tissue is washed 3 times and allowed to re-equilibrate to basal rate. The test compound is added to the tissue bath at the desired final concentration. Thirty minutes after addition of the compound, a fresh histamine dose response curve is again obtained. Then the response to histamine in the presence of antagonist is compared to the histamine control response. This procedure is repeated, using fresh tissues, for each concentration of antagonist tested. The result is expressed as the apparent dissociation constant ($pA_2$) of the $H_2$ antagonist as determined by standard procedures. Cimetidine is used as the standard for this test.

The results for a series of compounds of the invention are as follows:

| Compound or Example No. | $pA_2$ Value |
|---|---|
| Cimetidine | 6.5 |
| 1 | 7.0 |
| 2 | 8.1 |
| 3 | 8.7 |
| 4 | 6.6 |
| 5 | 7.3 |
| 6 | 7.7 |
| 7 | 7.5 |
| 8 | 7.7 |
| 9 | 6.7 |
| 10 | 7.3 |
| 11 | 7.1 |
| 12 | 8.0 |
| 16 | <7.0 |
| 18 | 7.8 |
| 19 | 6.7 |
| 20 | 7.6 |
| 21 | 7.1 |
| 22 | 8.2 |
| 23 | 7.6 |
| 24 | 8.24 |
| 25 | 7.39 |
| 26 | 7.7 |
| 27 | 7.35 |
| 28 | 7.6 |
| 29 | 7.16 |
| 30 | 7.2 |
| 31 | 7.2 |
| 32 | 7.2 |
| 34 | 8.0 |
| 35 | $1.4 \times 10^{-8}M$* |
| 36 | $4.8 \times 10^{-8}M$* |
| 38 | 7.63 |
| 39 | $1.0 \times 10^{-9}M$* |
| 40 | $1.0 \times 10^{-7}M$* |
| 41 | $5.94 \times 10^{-9}M$* |

*These values are the $K_B$ values for the compounds tested, and the $K_B$ differs from the $A_2$ value only by the fact that the $A_2$ value reflects the results of three experiments, while the $K_B$ value represents the result of only one experiment.

The results show that the compounds of the invention are extremely active $H_2$ antagonists, being significantly more active than the standard compound cimetidine.

EXAMPLE 43

The procedure for testing gastric secretion in the rat, a modification of the procedure of Shay et al., *Gastroenterology*, 26, 906-13 (1954) is carried out as follows:

Male Charles River rats weighing 200-300 grams are deprived of food but not water for 24 hours prior to use. Water is, however, withheld during the experiment. The rats are weighed, anesthetized, and the pylorus ligated according to the method of Shay et al. Treatment or vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or hemolysis are eliminated. An aliquot of each is frozen for later analysis of $Na^+$, $K^+$ and $Cl^-$ concentration. The pH is measured and 1 ml. of gastric juice is titrated with 0.1N NaOH to a pH of 7.0-7.4. Titratable acid output is calculated in microequivalents and the percent inhibition of acid output is calculated as follows:

$$\% \text{ Inhibition of Acid Output} = \frac{\text{Acid Output (control)} - \text{Acid Output (Drug)}}{\text{Acid Output (control)}} \times 100$$

The test results for some of the compounds of the invention and for the known $H_2$ antagonists ranitidine and tiotidine are as follows:

| Compound of Example No. | Dose (mg/kg) | % Inhibition |
|---|---|---|
| 1 | 4 | 79 |
| 16 | 32 | 39 |
| 18 | 32 | 90 |
|  | 16 | 89 |
|  | 8 | 67 |
| 19 | 32 | 78 |
|  | 16 | 52 |
| 20 | 2 | 50 |
| 21 | 32 | 72 |
| 22 | 32 | 68 |
|  | 16 | 53 |
|  | 8 | 62 |
|  | 4 | 42 |
| 24 | 8 | 50 |
| 25 | 4 | 48 |
| 28 | 32 | 49 |
|  | 16 | 75 |
| 29 | 32 | 50 |
| 35 | 32 | 55 |
| 36 | 32 | 84 |
| 37 | 32 | 38 |
| 38 | 16 | 93 |
|  | 4 | 52 |
|  | 1 | 34 |
| 39 | 16 | 87 |
| 41 | 8 | 91 |
|  | 4 | 87 |

-continued

| Compound of Example No. | Dose (mg/kg) | % Inhibition |
|---|---|---|
|  | 1 | 84 |
|  | 0.5 | 37 |
| ranitidine | 4 | 43 |
| tiotidine | 4 | 16 |

The results show the compounds of the invention to have significant activity in inhibiting gastric acid secretion.

EXAMPLE 44

The procedure for testing the ability of the compounds of the invention to inhibit the secretion of acidic gastric juice in dogs is as follows:

A female pure bred beagle (7–10 kg) having Pavlov gastric pouches is fasted overnight with water ad lib. The animal is orally dosed and thirty minutes later it is fed to induce gastric acid secretions. Gastric acid samples are then collected every 15 minutes. The volume of each sample is measured and aliquots are titrated to neutrality with 0.1N NaOH to determine acid concentration. The results are reported as the dose at which there is obtained a 50% inhibition of the total gastric acid output ($ID_{50}$).

The results for some compounds of the invention and the known $H_2$ antagonists cimetidine and ranitidine are presented below:

| Compound of Example No. | $ID_{50}$(mg/kg) |
|---|---|
| 1 | 0.8 |
| 18 | 1.2 |
| 20 | 1.4 |
| 24 | 1.2 |
| 38 | 2.0 |
| 41* | 0.25 |
| cimetidine | 6.0 |
| ranitidine | 2.3 |

*This compound reduced gastric acid secretions in the dog by 82% at a dose of 1 mg/kg.

The results show that the compounds of the invention are extremely active in reducing gastric acid secretions in the dog at very low dosage levels, and that the levels are below the levels at which the same reduction in gastric acid secretion is attained by the known $H_2$ antagonists cimetidine and ranitidine.

What is claimed is:

1. A compound having the formula:

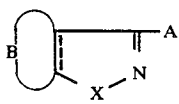

wherein
B is a moiety having the formula:

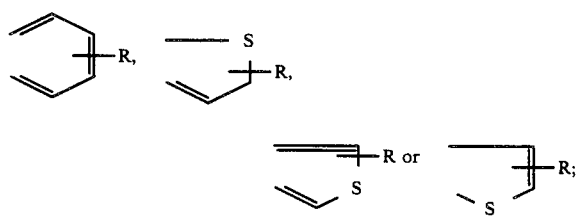

R is hydrogen, mono- or dihalo, amino, nitro, cyano, hydroxy, trifluoromethyl, mercapto, lower alkyl, lower alkoxy, alkanoyl of 2–5 carbon atoms, lowercycloalkyl, carboxy, alkoxycarbonyl of 2–7 carbon atoms, mono- or di-loweralkyl substituted amino, alkanoylamino of 2–5 carbon atoms, lower alkyl thio, loweralkylsulfonyl, sulfamoyl, lower alkyl substituted sulfamoyl, phenyl or phenyl substituted with halo, lower alkyl, lower alkoxy, trifluoromethyl, hydroxy, amino, cyano or nitro;

X is $SO_2$, SO, S or C=O;

and

A is an amine selected from the group:

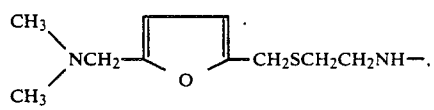

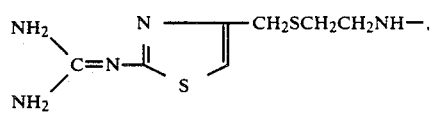

or

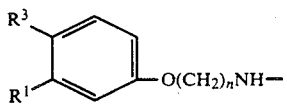

wherein $R^1$ is hydrogen or $R^2CH_2$ wherein $R^2$ is mono- or diloweralkylamino, mono- or di-N-loweralkylaminoloweralkyl, (2-furyl)methylamino, benzylamino, lowercycloalkylamino, 1-pyrrolidinyl, 1-piperidinyl, 1-hexahydroazepinyl, 1-octahydroazocinyl, 3-tetrahydrothiazolyl, 4-morpholinyl or 4-thiomorpholinyl; $R^3$ is hydrogen or (1-piperidinyl)methyl with the proviso that when $R^3$ is (1-piperidinyl)methyl, $R^1$ is hydrogen; n is 1 to 4, or a pharmacologically acceptable salt thereof.

2. The compound of claim 1, wherein the moiety B is

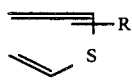

3. The compound of claim 1, having the name N-[2-[[[5-[(dimethylamino)methyl]-2-furanyl]methyl]thio]ethyl]-1,2-benzisothiazol-3-amino 1,1-dioxide.

4. The compound of claim 1, having the name N-[3-[3-[(1-piperidinyl)methyl]phenoxy]propyl]-1,2-benzisothiazol-3-amine 1,1-dioxide.

5. The compound of claim 1, having the name [4-[[[-2-[(1,2-benzisothiazol-3-yl)amino]ethyl]thio]methyl]-2-thiazol-yl]guanidine S',S'-dioxide.

6. The compound of claim 1, having the name 3-[[3-[3-[(1-piperidinyl)methyl]phenoxy]propyl]amino]]-1H-isoindol-1-one.

7. The compound of claim 1, having the name N-[3-[3-[(1-piperidinyl)methyl)]phenoxy]propyl]-6-nitro-1,2-benzisothiazol-3-amine 1,1-dioxide.

8. The compound of claim 1, having the name N-[3-[3-[(1-piperidinyl)methyl]phenoxy]propyl]-6-amino-1,2-benzisothiazol-3-amine 1,1-dioxide.

9. The compound of claim 1, having the name N-[3-[3-[(1-piperidinyl)methyl]phenoxy]propyl]-6-chloro-benzisothiazol-3-amine 1,1-dioxide.

10. The compound of claim 1, having the name N-[3-[3-[(1-piperidinyl)methyl]phenoxy]propyl]-6-fluoro-1,2-benzisothiazol-3-amine 1,1-dioxide.

11. The compound of claim 1, having the name N-[3-[3-[(1-piperidinyl)methyl]phenoxy]propyl]-5,6-dichloro-1,2-benzisothiazol-3-amine 1,1-dioxide.

12. The compound of claim 1, having the name N-[3-[3-[(1-piperidinyl)methyl]phenoxy]propyl]-5-methyl-1,2-benzisothiazol-3-amine 1,1-dioxide.

13. The compound of claim 1, having the name N-[3-[3-[(1-piperidinyl)methyl]phenoxy]propyl]-5-chloro-1,2-benzisothiazol-3-amine 1,1-dioxide.

14. The compound of claim 1, having the name N-[3-[3-[(1-piperidinyl)methyl]phenoxy]propyl]-5-methoxy-1,2-benzisothiazol-3-amine 1,1-dioxide.

15. The compound of claim 1, having the name N-[3-[3-[(1-piperidinyl)methyl]phenoxy]propyl]-6-sulfamoyl-1,2-benzisothiazol-3-amine 1,1-dioxide.

16. The compound of claim 1, having the name N-[3-[3-[(1-piperidinyl)methyl]phenoxy]propyl]-6-bromo-1,2-benzisothiazol-3-amine 1,1-dioxide.

17. The compound of claim 1, having the name N-[3-[3-[(1-piperidinyl)methyl]phenoxy]propyl]-5-fluoro-1,2-benzisothiazol-3-amine 1,1-dioxide.

18. The compound of claim 1, having the same N-[3-[3-(4-morpholinylmethyl)phenoxy]propyl]-1,2-benzisothiazol-3-amine 1,1-dioxide.

19. The compound of claim 1, having the name N-[3-[3-[(dipropylamino)methyl]phenoxy]propyl]-1,2-benzisothiazol-3-amine 1,1-dioxide.

20. The compound of claim 1, having the name N-[3-[3-[(diethylamino)methyl]phenoxy]propyl]-1,2-benzisothiazol-3-amine 1,1-dioxide.

21. The compound of claim 1, having the name N-[3-[3-(1-pyrrolidinylmethyl)phenoxy]propyl]-1,2-benzisothiazol-3-amine, 1,1-dioxide.

22. The compound of claim 1, having the name N-[3-[3-[(dimethylamino)methyl]phenoxy]propyl]-1,2-benzisothiazol-3-amine 1,1-dioxide.

23. The compound of claim 1, having the name N-[3-[3-[(dibutylamino)methyl]phenoxy]propyl]-1,2-benzisothiazol-3-amine 1,1-dioxide.

24. The compound of claim 1, having the name N-[3-[3-[(4-thiomorpholinyl)methyl]phenoxy]propyl]-1,2-benzisothiazol-3-amine 1,1-dioxide.

25. The compound of claim 1, having the name N-[3-[3-[(hexahydro-1H-azepin-1-yl)methyl]phenoxy]propyl]-1,2-benziosothiazol-3-amine 1,1-dioxide.

26. The compound of claim 1, having the name N-[3-[3-[(3-thiazolidinyl)methyl]phenoxy]propyl]-1,2-benzisothiazol-3-amine 1,1-dioxide.

27. The compound of claim 1, having the name N-[3-[3-[(octahydro-1(2H)-azocinyl)methyl]phenoxy]propyl]-1,2-benzisothiazol-3-amine 1,1-dioxide.

28. The compound of claim 1, having the name N-[3-[3-[(cyclohexylamino)methyl]phenoxy]propyl]-1,2-benzisothiazol-3-amine 1,1-dioxide.

29. The compound of claim 1, having the name N-[3-[3-[(cyclopentylamino)methyl]phenoxy]propyl]-1,2-benzisothiazol-3-amine 1,1-dioxide.

30. The compound of claim 1, having the name N-[3-[3-[[[(2-furanyl)methyl]amino]methyl]phenoxy]propyl]-1,2-benzisothiazol-3-amine 1,1-dioxide.

31. The compound of claim 1, having the name N-[3-[3-[(benzylamino)methyl]phenoxy]propyl]-1,2-benzisothiazol-3-amine 1,1-dioxide.

32. The compound of claim 1, having the name N-[3-[3-[[bis(2-methylpropyl)amino]methyl]phenoxy]propyl]-1,2-benzisothiazol-3-amine 1,1-dioxide.

33. The compound of claim 1, having the name N-[3-[3-[(butylamino)methyl]phenoxy]propyl]-1,2-benzisothiazol-3-amine 1,1-dioxide.

34. The compound of claim 1, having the name N-[3-[3-[(methylpentylamino)methyl]phenoxy]propyl]-1,2-benzisothiazol-3-amine 1,1-dioxide.

35. The compound of claim 1, having the name N-[3-[3-[(butylpropylamino)methyl]phenoxy]propyl]-1,2-benzisothiazol-3-amine 1,1-dioxide.

36. The compound of claim 1, having the name N-[3-[3-[(butylmethylamino)methyl]phenoxy]propyl]-1,2-benzisothiazol-3-amine 1,1-dioxide.

37. The compound of claim 1, having the name N-[3-[3-[(dipentylamino)methyl]phenoxy]propyl]-1,2-benzisothiazol-3-amine 1,1-dioxide.

38. The compound of claim 1, having the name N-[3-[4-[(1-piperidinyl)methyl]phenoxy]propyl]-1,2-benzisothiazol-3-amine 1,1-dioxide.

39. The compound of claim 1, having the name N-[2-[[[5-[(dimethylamino)methyl]-2-furanyl]methyl]thio]ethyl]thieno[3,4-d]isothiazole-3-amine 1,1-dioxide.

40. The compound of claim 1, having the name [4-[[[2-[(thieno[3,4-d]isothiazol-3-yl)amino]ethyl]thio]methyl]-2-thiazolyl guanidine S',S'-dioxide.

41. The compound of claim 1, having the name N-[2-[3-(1-piperidinylmethyl)phenoxy]ethyl]thieno[3,4-d]isothiazol-3-amine 1,1-dioxide.

* * * * *